(12) United States Patent
Carroll

(10) Patent No.: US 11,406,827 B2
(45) Date of Patent: Aug. 9, 2022

(54) SPINAL CORD STIMULATION WITH INTERFERENTIAL CURRENT USING MULTIPLE BEAT SIGNALS

(71) Applicant: Meagan Medical, Inc., Vancouver, WA (US)

(72) Inventor: William J. Carroll, LaCenter, WA (US)

(73) Assignee: Meagan Medical, Inc., Vancouver, WA (US)

( * ) Notice: Subject to any disclaimer, the term of this patent is extended or adjusted under 35 U.S.C. 154(b) by 0 days.

(21) Appl. No.: 17/081,129

(22) Filed: Oct. 27, 2020

(65) Prior Publication Data
US 2021/0138245 A1 May 13, 2021

Related U.S. Application Data

(60) Provisional application No. 62/933,069, filed on Nov. 8, 2019.

(51) Int. Cl.
*A61N 1/36* (2006.01)
*A61N 1/05* (2006.01)

(52) U.S. Cl.
CPC ....... *A61N 1/36062* (2017.08); *A61N 1/0551* (2013.01); *A61N 1/36067* (2013.01);
(Continued)

(58) Field of Classification Search
CPC .............. A61N 1/0551; A61N 1/36062; A61N 1/36125; A61N 1/36171; A61N 1/36196;
(Continued)

(56) References Cited

U.S. PATENT DOCUMENTS

2004/0167584 A1* 8/2004 Carroll ............... A61N 1/36185
607/46
2007/0038255 A1* 2/2007 Kieval .................... A61N 1/05
607/4

(Continued)

FOREIGN PATENT DOCUMENTS

WO    WO 2002/009808    2/2002

OTHER PUBLICATIONS

International Search Report and Written Opinion prepared by the European Patent Office in International Application No. PCT/US20/57462 dated Jan. 27, 2021.

*Primary Examiner* — Carl H Layno
*Assistant Examiner* — Anh-Khoa N Dinh
(74) *Attorney, Agent, or Firm* — McDonnell Boehnen Hulbert & Berghoff LLP

(57) ABSTRACT

An example method for spinal cord stimulation treatment includes positioning eight implantable electrodes to a dura matter in an epidural space proximate to a subject's spinal cord so that (i) a first circuit is created between a first and second electrode on a first channel, (ii) a second circuit is created between a third and fourth electrode on a second channel, (iii) a third circuit is created between a fifth and sixth electrode on a third channel, and (iv) a fourth circuit is created between a seventh and eighth electrode on a fourth channel, transmitting signals through the first and second circuits that interfere to produce a first beat signal, transmitting signals through the third and fourth circuits that interfere to produce a second beat signal, and interaction of the first and second beat signals results in a combined beat signal proximate to the subject's spinal cord.

20 Claims, 10 Drawing Sheets

(52) U.S. Cl.
CPC ..... *A61N 1/36071* (2013.01); *A61N 1/36125* (2013.01); *A61N 1/36171* (2013.01); *A61N 1/36196* (2013.01)

(58) Field of Classification Search
CPC ............ A61N 1/36014; A61N 1/36017; A61N 1/36021; A61N 1/36025; A61N 1/0553; A61N 1/0556; A61N 1/0558; A61N 1/0563; A61N 1/0565; A61N 1/057; A61N 2001/0585; A61N 1/10; A61N 1/32
See application file for complete search history.

(56) References Cited

U.S. PATENT DOCUMENTS

| | | | |
|---|---|---|---|
| 2016/0220828 A1* | 8/2016 | Yan Poon | ............ A61N 1/3756 |
| 2017/0036029 A1* | 2/2017 | Carroll | ............... A61N 1/36071 |
| 2019/0262616 A1 | 8/2019 | Carroll | |

* cited by examiner

200 ⟶

```
┌─────────────────────────────────────────────────────────────────────┐
│ POSITIONING AT LEAST EIGHT IMPLANTABLE ELECTRODES TO A DURA         │
│ MATTER IN AN EPIDURAL SPACE PROXIMATE TO A SUBJECT'S SPINAL CORD    │
│ AT PREDETERMINED LOCATIONS SO THAT (I) A FIRST CIRCUIT IS CREATED   │
│ BETWEEN A FIRST ELECTRODE AND A SECOND ELECTRODE OF THE EIGHT       │
│ IMPLANTABLE ELECTRODES ON A FIRST CHANNEL, (II) A SECOND CIRCUIT IS │
│ CREATED BETWEEN A THIRD ELECTRODE AND A FOURTH ELECTRODE OF THE     │
│ EIGHT IMPLANTABLE ELECTRODES ON A SECOND CHANNEL, (III) A THIRD     │  202
│ CIRCUIT IS CREATED BETWEEN A FIFTH ELECTRODE AND A SIXTH            │
│ ELECTRODE OF THE EIGHT IMPLANTABLE ELECTRODES ON A THIRD            │
│ CHANNEL, AND (IV) A FOURTH CIRCUIT IS CREATED BETWEEN A SEVENTH     │
│ ELECTRODE AND AN EIGHTH ELECTRODE OF THE EIGHT IMPLANTABLE          │
│ ELECTRODES ON A FOURTH CHANNEL                                      │
└─────────────────────────────────────────────────────────────────────┘
                                    ↓
┌─────────────────────────────────────────────────────────────────────┐
│ TRANSMITTING FIRST SIGNALS THROUGH THE FIRST CIRCUIT AND THE        │
│ SECOND CIRCUIT SO THAT THE FIRST SIGNALS INTERFERE WITH EACH        │  204
│ OTHER TO PRODUCE A FIRST BEAT SIGNAL                                │
└─────────────────────────────────────────────────────────────────────┘
                                    ↓
┌─────────────────────────────────────────────────────────────────────┐
│ TRANSMITTING SECOND SIGNALS THROUGH THE THIRD CIRCUIT AND THE       │
│ FOURTH CIRCUIT SO THAT THE SECOND SIGNALS INTERFERE WITH EACH       │  206
│ OTHER TO PRODUCE A SECOND BEAT SIGNAL                               │
└─────────────────────────────────────────────────────────────────────┘
```

FIG. 7

SPINAL CORD STIMULATION WITH INTERFERENTIAL CURRENT USING MULTIPLE BEAT SIGNALS

CROSS-REFERENCE TO RELATED APPLICATION

The present disclosure claims priority to U.S. provisional patent application No. 62/933,069 filed on Nov. 8, 2019, the entire contents of which are herein incorporated by reference.

FIELD

The present disclosure is generally related to spinal cord stimulation and, more particularly, is related to an apparatus and method for the electrical stimulation of the spinal cord using an interferential current pattern for treating certain conditions.

BACKGROUND

Electrical stimulation of the posterior spinal cord, spinal cord stimulation (SCS), has developed into an effective therapeutic tool for treating chronic pain conditions. However, very little is known about the sites of activation or the neural mechanisms evoked by SCS that relieve pain and promote changes in the function of somatic and visceral structures.

Spinal Cord Stimulation is most commonly used for patients with chronic intractable pain syndromes. It has also been useful for treating movement disorders and is occasionally used following head injuries. However, one complication with SCS is that of accommodation or habituation to the stimulation signal. Companies that manufacture spinal stimulation devices have developed complex stimulation programs and devoted chapters on techniques to reduce the problem of accommodation during SCS (Alfano S, Darwin J, Picullel B: Spinal Cord Stimulation, Patient Management Guidelines for Clinicians, Medtronic, Inc.). Accommodation is when the body habituates or becomes accustomed to an activity or signal and then starts to ignore or "tune it out". By varying the signal or keeping the focal point of the signal moving, accommodation can be minimized.

Dorsal Column Stimulation (DCS) or SCS using an electrical current pattern has shown to be a cost benefit in treating chronic pain disorders in patients (Dorsal column stimulation: cost to benefit analysis; *Acta Neurochir Suppl (Wien)*, 52( ): 121-3, 1991).

SCS stimulates the dorsal column in a somewhat superficial manner as pointed out by Holsheimer (Holsheimer J: Which Neuronal Elements are activated Directly by Spinal Cord Stimulation, *Neuromodulation*, Volume 5, Number 1: 25-31, 2002). The electrodes are normally attached to the dura matter in the epidural space, and most of the current distribution remains in the cerebrospinal fluid (CSF) and does not project deeply into the dorsal column.

Thus, traditional SCS stimulation has limited application because of the spread of the stimulating electrical field within the CSF as intensity of stimulation increases. This is due to the highly conductive nature of the CSF as compared to the less conductive nature of the spinal cord tissue itself. Thus, traditional SCS stimulation is "amplitude limited" to a relatively narrow surface area of the spinal cord. Frequently, patient satisfaction with electrical stimulation is compromised by the recruitment of adjacent neuronal structures that, when activated, can create discomfort, motor contractions, and outright pain. The efficacy of the therapy is thus limited.

Thus, a heretofore unaddressed need exists in the industry to address the aforementioned deficiencies and inadequacies with regard to accommodation or habituation to the spinal cord stimulation signal when used in the treatment of chronic pain syndromes.

SUMMARY

Within examples, using interferential stimulation with implantable leads to decrease the problem of accommodation is advantageous. Providing an interferential component to the electrode array of the SCS and using a double parallel circuit arrangement allows interaction of two beat signals, and the resultant additive effect of the combined beat signal produces deeper penetration of the signal and a higher resultant amplitude at the stimulation site. The interferential current would recruit larger numbers of dorsal column fibers and provide greater levels of pain relief and benefit to intractable pain patients.

Within examples, a method for spinal cord stimulation treatment using electrical stimulation of the spinal cord is described. The method comprises positioning at least eight implantable electrodes to a dura matter in an epidural space proximate to a subject's spinal cord at predetermined locations so that (i) a first circuit is created between a first electrode and a second electrode of the eight implantable electrodes on a first channel, (ii) a second circuit is created between a third electrode and a fourth electrode of the eight implantable electrodes on a second channel, (iii) a third circuit is created between a fifth electrode and a sixth electrode of the eight implantable electrodes on a third channel, and (iv) a fourth circuit is created between a seventh electrode and an eighth electrode of the eight implantable electrodes on a fourth channel. The method also comprises transmitting first signals through the first circuit and the second circuit so that the first signals interfere with each other to produce a first beat signal, and transmitting second signals through the third circuit and the fourth circuit so that the second signals interfere with each other to produce a second beat signal. The method also comprises interaction of the first beat signal and the second beat signal results in a combined beat signal proximate to the subject's spinal cord.

In another example, an electrical stimulator for spinal cord stimulation treatment is described that comprises an interferential current generator which generates an interferential alternating current output comprising first signals and second signals, and at least eight implantable electrodes. Each electrode has a first and a second end, and the first ends are coupled to the interferential current generator and the second ends are configured to be implanted to a dura matter in an epidural space at predetermined locations proximate to a subject's spinal cord so that (i) a first circuit is created between a first electrode and a second electrode of the eight implantable electrodes on a first channel, (ii) a second circuit is created between a third electrode and a fourth electrode of the eight implantable electrodes on a second channel, (iii) a third circuit is created between a fifth electrode and a sixth electrode of the eight implantable electrodes on a third channel, and (iv) a fourth circuit is created between a seventh electrode and an eighth electrode of the eight implantable electrodes on a fourth channel. First signals are transmitted through the first circuit and the second circuit so that the first signals interfere with each other to produce a first beat signal, and second signals are transmitted through the third circuit and the fourth circuit so that the second signals interfere with each other to produce a second beat signal. Interaction of the first beat signal and the second beat signal results in a combined beat signal proximate to the subject's spinal cord.

These as well as other aspects, advantages, and alternatives will become apparent to those of ordinary skill in the art by reading the following detailed description, with reference where appropriate to the accompanying drawings.

BRIEF DESCRIPTION OF THE DRAWINGS

Many aspects of the disclosure can be understood with reference to the following drawings. The components in the drawings are not necessarily to scale. Moreover, in the drawings, like reference numerals designate corresponding parts throughout the several views.

FIG. 7 shows a flowchart of an example of a method for spinal cord stimulation treatment using electrical stimulation of the spinal cord, according to an example embodiment.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Examples described herein provide an apparatus and method for electrical stimulation of the spinal cord. Within examples, an electrical stimulator is provided for the treatment of intractable pain syndromes that includes implantable electrodes implanted to a dura mater proximate to a subject's spinal cord, and interferential stimulation is used to produce beat frequency signals, that each interact to produce a combined beat signal such that a majority of the combined beat frequency signal is directionally distributed and controlled to avoid stimulating adjacent and/or inappropriate neuronal targets within the spinal canal, thereby creating a far more efficacious neuro-stimulation field in the treatment of pain. In other examples, a majority of the combined beat frequency signal is directionally distributed and controlled to avoid remaining in and shunting through the cerebrospinal fluid proximate to the subject's spinal cord.

An effective area of stimulation is controlled by the quantity of electrodes, positioning of the electrodes and electrode interference pattern orientation. Thus, the combined beat frequency signal can be directionally controlled.

This type of current (interferential) provides improved directional control, decreased accommodation or habituation and increased depth of penetration in comparison to other standard implantable stimulation systems and their accompanying surgical leads. The amplitudes of the outputs in the respective circuits may be modulated to increase the area of targeted stimulation. Interferential current allows improved directional control and depth of penetration in comparison to other stimulation techniques. Thus, by generating the combined beat frequency signal, the resultant additive signal is directionally controlled to avoid cerebrospinal fluid proximate to the subject's spinal cord.

Within examples, to target specific areas of the spinal cord using modulation of the circuit outputs, the resultant combined beat frequency signal would be directionally controlled and/or depths of penetration are controlled.

Figure 1:
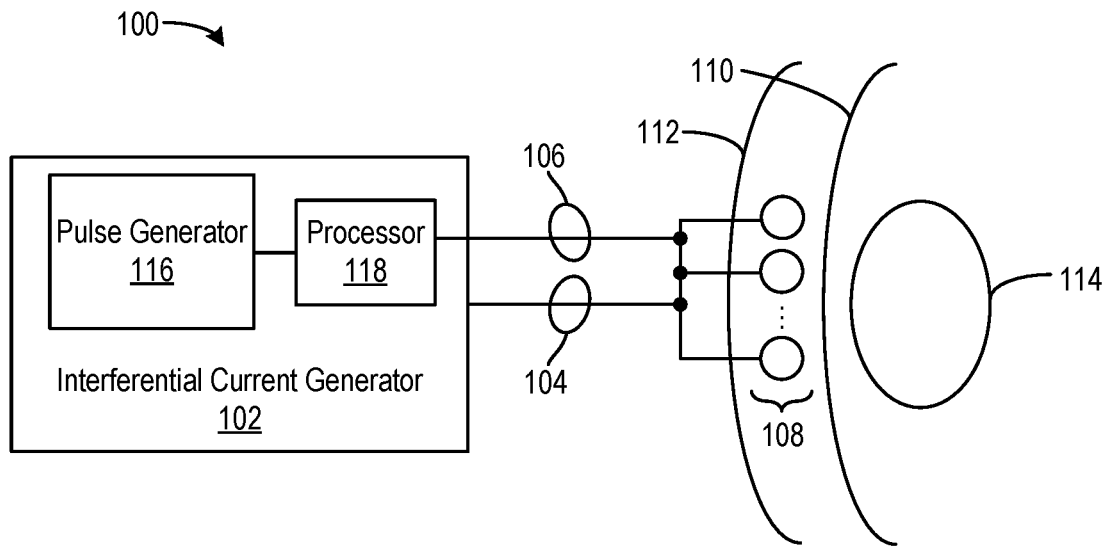
FIG. 1 illustrates an example of an electrical stimulator for spinal cord stimulation treatment, according to an example implementation.

FIG. 1 illustrates an example of an electrical stimulator 100 for spinal cord stimulation treatment, according to an example implementation. The electrical stimulator 100 includes an interferential current generator 102 which generates an interferential alternating current output comprising first signals 104 and second signals 106. The electrical stimulator 100 also includes at least eight implantable electrodes 108, and each electrode has a first and a second end. The first ends are coupled to the interferential current generator 102 and the second ends are configured to be implanted to a dura matter 110 in an epidural space 112 at predetermined locations proximate to a subject's spinal cord 114 so that (i) a first circuit is created between a first electrode and a second electrode of the eight implantable electrodes on a first channel, (ii) a second circuit is created between a third electrode and a fourth electrode of the eight implantable electrodes on a second channel, (iii) a third circuit is created between a fifth electrode and a sixth electrode of the eight implantable electrodes on a third channel, and (iv) a fourth circuit is created between a seventh electrode and an eighth electrode of the eight implantable electrodes on a fourth channel. The arrangements of the different circuits is shown in more detail in FIG. 3-5.

The first signals 104 are transmitted through the first circuit and the second circuit so that the first signals interfere with each other to produce a first beat signal, and the second signals 106 are transmitted through the third circuit and the fourth circuit so that the second signals interfere with each other to produce a second beat signal. Interaction of the first beat signal and the second beat signal results in a combined beat signal proximate to the subject's spinal cord 114.

An interferential current recruits larger numbers of dorsal column fibers and provides greater levels of pain relief. In some examples, as a result of recruiting larger numbers of dorsal column fibers by using interferential current and by generating a beat frequency signal, the patients could potentially experience greater levels of pain relief.

In some examples, the interferential current generator 102 includes a pulse generator 116 that generates digital signal pulses, and a processor 118 connected to the pulse generator 116 that processes the digital signal pulses to approximate a sine-wave-like output waveform for the first signals 104 and the second signals 106. For example, the output may be a sinewave, pseudo sinewave, or some sine-wave-like continuous waveform that are in-phase. The processor 118 then transmits the sine-wave-like output waveform as the first signals 104 and the second signals 106. The processor 118 may be or include a field-programmable gate array used to shape multiple pulsatile waveforms to approximate the output of a sine-wave generator instead of or in addition to a digital signal processor. The FPGA is an integrated circuit that can be programmed in the field after it is manufactured and allows its user to adjust the circuit output as desired. Thus, in an alternative example, the processor 118 may be replaced with the FPGA. An FPGA device can allow for complex digital signal processing applications such as finite impulse response filters, forward error correction, modulation-demodulation, encryption and applications.

The pulse generator 116 generates individual pulses of differing widths and resultant amplitudes. In some examples, the pulse width is set at 210 microseconds, but can range from 50-600 microseconds. When those differing pulses are driven into a transformer (not shown), the pseudo-sine-wave is produced. The pulse generator 116 is connected to the processor 118 and supplies the pulsed digital signal output to the processor 118. Within examples, a range of output of the first, second, third, and fourth electrical circuits created is about 0-11 volts per circuit, depending on the patient's needs for pain treatment.

Thus, the pulse generator 116 generates an interferential output including the first signals 104 and the second signals 106 having different first and second frequencies. Pairs of the implantable electrodes 108 carry one of the first signals 104 and the second signals 106. Where the first circuit (created between a first electrode and a second electrode) and second circuit (created between a third electrode and a fourth electrode) interfere, the resultant beat frequency (which may be between 1 and 250 beats/second) will be a difference between frequencies of the two circuits, and the amplitude will be additive and greater than either circuit alone. Within other examples, the resultant beat frequency signal may have a frequency within a range of more than 250 Hz to about 15,000 Hz.

Similarly, where the third circuit (created between a fifth electrode and a sixth electrode) and fourth circuit (created between a seventh electrode and an eighth electrode) interfere, the resultant beat frequency (which may be between 1 and 250 beats/second) will be a difference between frequencies of the two circuits, and the amplitude will be additive and greater than either circuit alone. Within other examples, the resultant beat frequency signal may have a frequency within a range of more than 250 Hz to about 15,000 Hz.

Subsequently, interaction of the first beat signal and the second beat signal results in a combined beat signal proximate to the subject's spinal cord 114.

Figure 2:
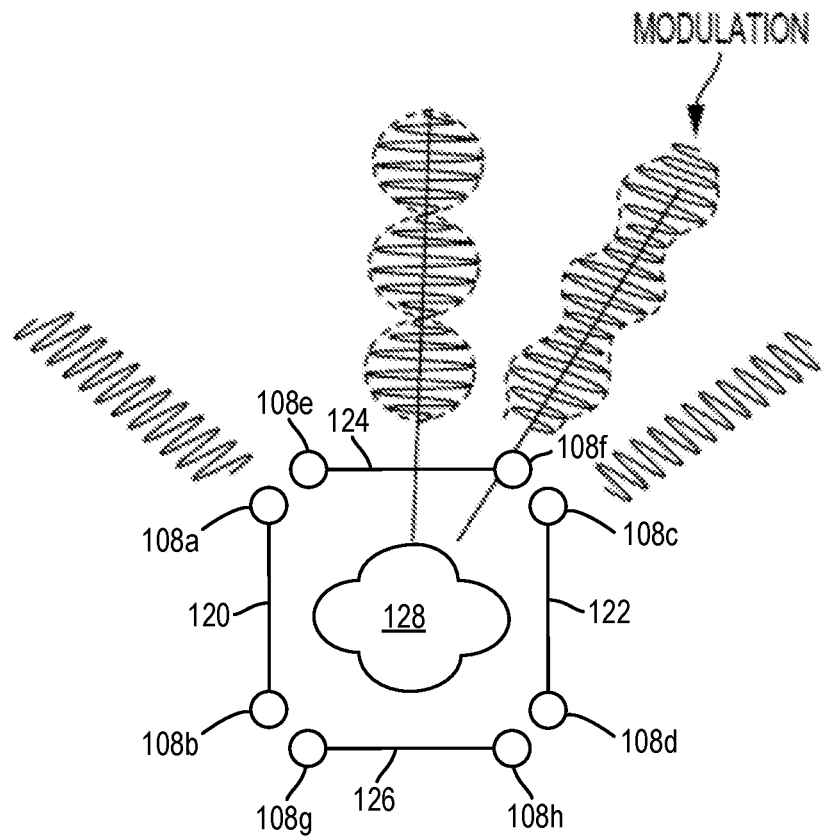
FIG. 2 illustrates an example perspective view of an interferential current pattern indicating a current intensity level and area of beat frequency formation, according to an example implementation.

FIG. 2 illustrates an example perspective view of an interferential current pattern indicating a current intensity level and area of beat frequency formation, according to an example implementation. In FIG. 2, a first circuit 120 is created between a first electrode 108a and a second electrode 108b of the eight implantable electrodes on a first channel, a second circuit 122 is created between a third electrode 108c and a fourth electrode 108d of the eight implantable electrodes on a second channel, a third circuit 124 is created between a fifth electrode 108e and a sixth electrode 108f of the eight implantable electrodes on a third channel, and a fourth circuit 126 is created between a seventh electrode 108g and an eighth electrode 108h of the eight implantable electrodes on a fourth channel.

The first pair of implantable electrodes 108a-b are shown positioned on the subject's spinal column at one set of corners of a target area 128, and the second pair of implantable electrodes 108c-d are then positioned at the other set of corners of the target area 128. Where the first circuit 120 and the second circuit 122 superimpose (overlap), a resultant beat frequency will be the difference between the frequencies of the two circuits, and the amplitude will be additive and greater than either circuit alone in the target area 128. Overlapping of the circuit fields is shown in FIGS. 3-5 below.

Similarly, where the third circuit 124 and the fourth circuit 126 superimpose (overlap), a resultant beat frequency will be the difference between the frequencies of the two circuits, and the amplitude will be additive and greater than either circuit alone in the target area 128. Subsequently, interaction of the two resultant beat frequencies results in a combined beat signal proximate to and/or within the subject's spinal cord in the target area 128.

Within examples, altering the target area 128 of the subject's spinal cord can be performed by modulating amplitudes of the signals, as shown in FIG. 2. Thus, multiple target areas of the spinal cord can be treated depending upon the quantity and placement of the pairs of electrodes, and by modulating the amplitudes of the outputs of the first and second circuits.

Figure 3:
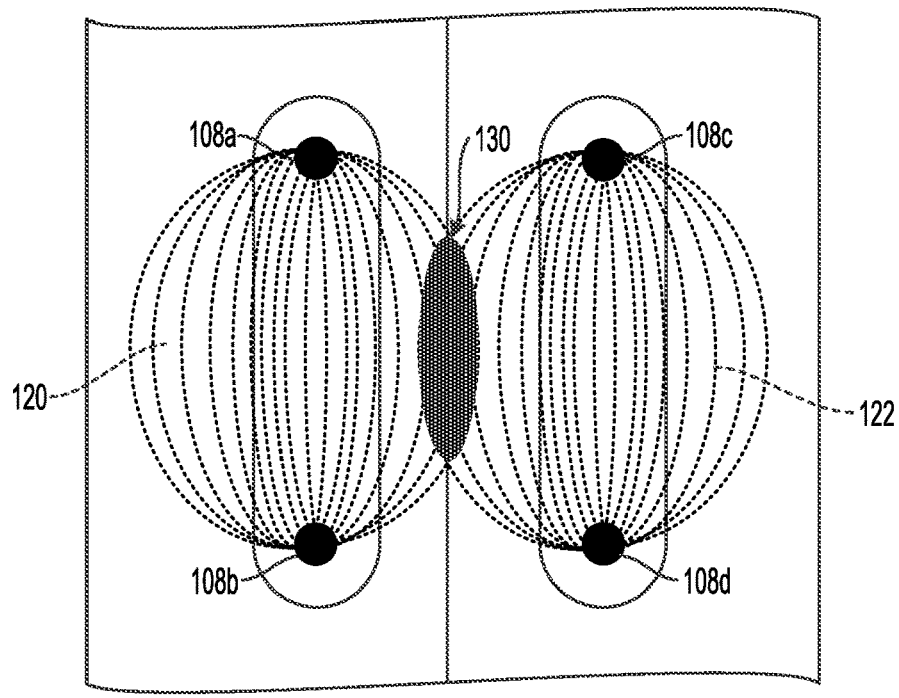
FIG. 3 is a perspective view illustrating an example effective area of stimulation resulting from the first pair of implantable electrodes and the second pair of implantable electrodes positioned in a parallel configuration such that the first circuit created between the first pair of implantable electrodes is parallel to the second circuit created between the second pair of implantable electrodes, according to an example implementation.
Figure 4:
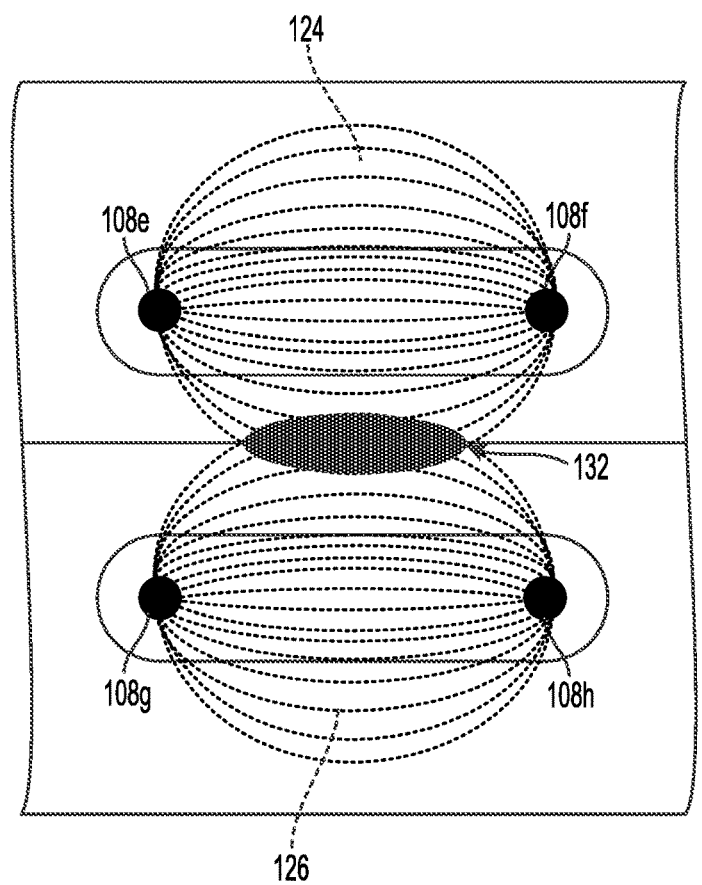
FIG. 4 is a perspective view illustrating another example effective area of stimulation resulting from the third pair of implantable electrodes and the fourth pair of implantable electrodes positioned in a parallel configuration such that the third circuit created between the third pair of implantable electrodes is parallel to the fourth circuit created between the fourth pair of implantable electrodes, according to an example implementation.

FIG. 3 is a perspective view illustrating an example effective area of stimulation resulting from the first pair of implantable electrodes 108a-b and the second pair of implantable electrodes 108c-d positioned in a parallel configuration such that the first circuit 120 created between the first pair of implantable electrodes 108a-b is parallel to the second circuit 122 created between the second pair of implantable electrodes 108c-d, according to an example implementation. The first signals 104 are transmitted through the first circuit 120 and the second circuit 122 so that the first signals 104 interfere with each other to produce a first beat signal 130. The first pair of implantable electrodes 108a-b and the second pair of implantable electrodes 108c-d are positioned vertically, such that the first circuit 120 and the second circuit 122 are arranged parallel to the spinal cord, for example. This may be considered or referred to as a vertical parallel bias arrangement.

FIG. 4 is a perspective view illustrating another example effective area of stimulation resulting from the third pair of implantable electrodes 108e-f and the fourth pair of implantable electrodes 108g-h positioned in a parallel configuration such that the third circuit 124 created between the third pair of implantable electrodes 108e-f is parallel to the fourth circuit 126 created between the fourth pair of implantable electrodes 108g-h, according to an example implementation. The second signals 106 are transmitted through the third circuit 124 and the fourth circuit 126 so that the second signals 106 interfere with each other to produce a second beat signal 132. The third pair of implantable electrodes 108e-f and the fourth pair of implantable electrodes 108g-h are positioned horizontally, such that the third circuit 124 and the fourth circuit 126 are arranged perpendicular to the spinal cord, for example. This may be considered or referred to as a horizontal parallel bias arrangement.

Beat frequency signals can be generated when the circuits are in a parallel configuration as shown in FIGS. 3 and 4, and there is an alignment of the generated fields. In a band where both fields align and overlap, there is a more focusable beat field that produces a controllable peak of amplitude within the modulation envelope. The area of overlap and concentration in the parallel electrode configuration can be maximized by biasing the electrodes so as to achieve aligned fields in the region of concentration (target). Biasing may be performed such that an anode and cathode of one pair of implantable electrodes are aligned vertically (longitudinal) and an anode and cathode of the other pair of implantable electrodes are aligned vertically (longitudinal) proximal to each other to form an area of overlap, and agreement with the beat frequency in between the two channels (circuits), as shown in FIGS. 3 and 4.

Thus, where the first circuit 120 and the second circuit 122 superimpose or overlap (and where the third circuit 124 and the fourth circuit 126 overlap), the resultant first beat signal 130 (and the second beat signal 132) will be the difference between the frequencies of the two circuits and the amplitude will be additive and greater than either circuit alone. Multiple levels of stimulation can be treated depending upon the electrode placement, pairing and modulation pattern selected. The range of output of the circuits may be from about 0 volts to about 11 volts per circuit depending on the patient's needs and the pulse width is commonly set at 210 microseconds but it could range from about 10-600 microseconds. The amplitude can be modulated in the respective circuits to increase the area of targeted stimulation.

In addition, biasing the pairs of implantable electrodes may be performed to cause the fields (e.g., first beat signal 130 and the second beat signal 132) to be unaligned for an untargeted region of concentration. Thus, in areas other than proximal to the target region, the beat frequency signal will be minimal and ineffective.

A horizontal distance between the two circuits in each of FIGS. 3 and 4 may be about between 1 mm and 5 mm, for example. Additionally, the pair of implantable electrodes may be positioned at a longitudinal (edge to edge) separation distance of about 2 mm to 10 mm, for example.

Within examples, using an electrical stimulator that includes electrodes implanted upon the dura mater with interferential currents produces a beat frequency signal that has deeper penetration than that possible using traditional SCS stimulation, and a majority of the beat frequency signal can be more precisely controlled in terms of direction and depth of tissue penetration proximate to the subject's spinal cord. Thus, interferential current may recruit larger numbers of dorsal column fibers and potentially provide greater levels of pain relief and benefit to intractable pain patients. Further, providing an interferential component to the electrode array of the SCS allows the interaction of the two signals such that the resultant additive effect of the beat frequency produces deeper penetration of the signal and a higher resultant amplitude at the stimulation site because only sub-threshold signals, of minimal biological consequence, remain in or shunt through the CSF. Because most of the current in conventional SCS remains in the CSF, it does not project deeply into the dorsal column. In contrast, providing an interferential component allows deeper penetration of the signal. Thus, the signal does not remain in the CSF.

Looking at the arrangements of the circuits in FIGS. 3 and 4 individually, resultant beat signals are created. Combining the arrangements of the circuits in FIGS. 3 and 4 results in a combined beat signal.

Figure 5A:
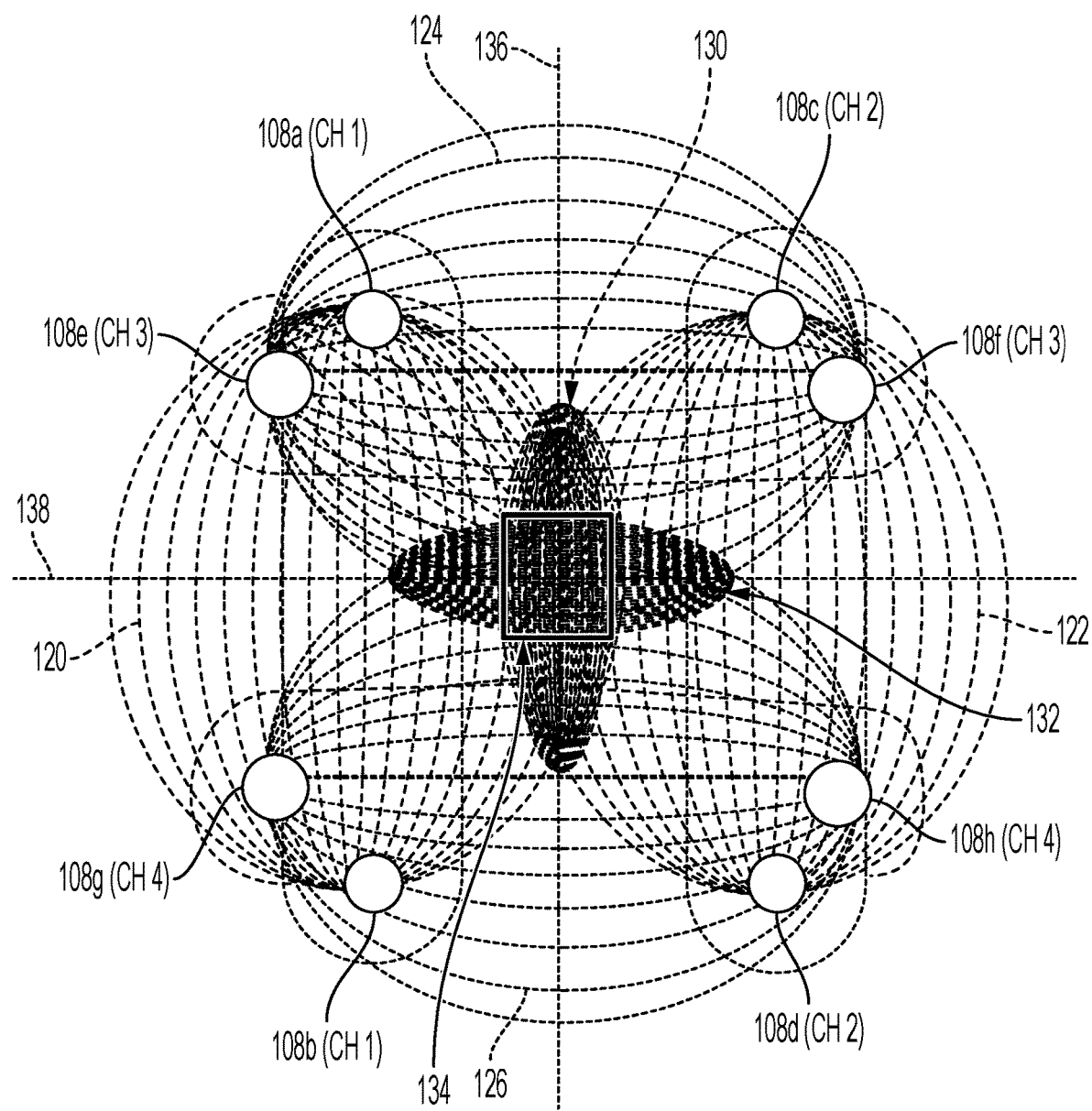
FIG. 5A is a perspective view illustrating an example effective area of stimulation resulting from a combination of the vertical and horizontal parallel arrangements of the first circuit and the second circuit combined with the third circuit and the fourth circuit, according to an example implementation.

FIG. 5A is a perspective view illustrating an example effective area of stimulation resulting from a combination of the vertical and horizontal parallel arrangements of the first circuit 120 and the second circuit 122 combined with the third circuit 124 and the fourth circuit 126, according to an example implementation. In FIG. 5A, the eight implantable electrodes 108a-h are implanted proximal to the spinal cord, and interaction of the first beat signal 130 and the second beat signal 132 results in a combined beat signal 134 proximate to the subject's spinal cord 114.

In FIG. 5A, the first circuit 120 and the second circuit 122 are arranged parallel to each other along a first plane 136, and the third circuit 124 and the fourth circuit 126 are arranged parallel to each other along a second plane 138. In this configuration, the first plane 136 is perpendicular to the second plane 138, or at least substantially perpendicular to the second plane 138 (allowing variances such as tolerances in which exact perpendicular arrangement is not required, e.g., ±5-10 degree variances). The first plane 136 may be a vertical plane that is parallel to the subject's spinal cord, and the second plane 138 may be a horizontal plane that is perpendicular to the subject's spinal cord. However, the first plane 136 and the second plane 138 may be arranged differently as well. Within examples, the first circuit 120, the second circuit 122, the third circuit 124, and the fourth circuit 126 are arranged in an approximate square configuration, and the combined beat signal 134 results in a center portion of the approximate square configuration. Approximate square configuration allows for tolerances or deviations from a square figure, such as non-parallel lines between electrodes, for example.

Using the configuration in FIG. 5A, the first circuit 120 is created between the pair of implantable electrodes 108a-b on a first channel, the second circuit 122 is created between the pair of implantable electrodes 108c-d on a second channel, the third circuit 124 is created between the pair of implantable electrodes 108e-f on a third channel, and the fourth circuit 126 is created between the pair of implantable electrodes 108g-h on a fourth channel.

In operation, transmitting the first signals 104 through the first circuit 120 and the second circuit 122 includes transmitting signals having a base frequency of about 15 kHz on the first channel, and transmitting signals having a base frequency of about 10 kHz on the second channel. Subsequently, signals on the first channel and the second channel interfere with each other to produce the first beat signal 130 having a beat frequency of about 5 kHz.

Similarly, transmitting the second signals 106 through the third circuit 124 and the fourth circuit 126 includes transmitting signals having a base frequency of about 20 kHz on the third channel, and transmitting signals having a base frequency of about 14.9 kHz on the fourth channel. Subsequently, signals on the third channel and the fourth interfere with each other to produce the second beat signal 132 having a beat frequency of about 5.1 kHz.

Following, in this example, interaction of the first beat signal 130 (having a beat frequency of about 5 kHz) and the second beat signal 132 (having a beat frequency of about 5.1 kHz) results in the combined beat signal 134 being about 100 Hz (5.1 kHz–5 kHz=100 Hz). An area of greatest beat current density could be moved in all directions depending on the relative amplitudes of the four channels.

Frequencies of signals may be transmitted through the first channel, the second channel, the third channel, and the fourth channel within ranges of about 0 to about 20,000 Hz, or any ranges than can result in the first beat signal 130 and the second beat signal 132 each having a frequency in a range of more than 250 Hz to about 15,000 Hz, or at least each having beat frequencies over 5 kHz, for example. The beat signal frequency results from interference of the two signals from the first channel and the second channel for the first beat signal 130, and from the third channel and the fourth channel for the second beat signal 132 (e.g., for a frequency of 2,000 Hz at the first channel creating a first field interfering with a second field generated by the second channel due to a frequency of 12,000 Hz results in a beat signal frequency of the first beat signal 130 of about 10 k Hz).

Based on combinations of the frequencies used and transmitted in the first channel, the second channel, the third channel, and the fourth channel, the first beat signal 130 and the second beat signal 132 may be in a range of more than 250 Hz to about 15,000 Hz. Other examples of either or both of the first beat signal 130 and the second beat signal 132 include a beat signal in a range of frequency between about 2,000 Hz to about 15,000 Hz, a range of frequency between about 3,000 Hz to about 15,000 Hz, a range of frequency between about 4,000 Hz to about 15,000 Hz, a range of frequency between about 5,000 Hz to about 15,000 Hz, a range of frequency between about 6,000 Hz to about 15,000 Hz, a range of frequency between about 7,000 Hz to about 15,000 Hz, a range of frequency between about 8,000 Hz to about 15,000 Hz, a range of frequency between about 9,000 Hz to about 15,000 Hz, a range of frequency between about 10,000 Hz to about 15,000 Hz, a range of frequency between about 11,000 Hz to about 15,000 Hz, a range of frequency between about 12,000 Hz to about 15,000 Hz, a range of frequency between about 13,000 Hz to about 15,000 Hz, a range of frequency between about 14,000 Hz to about 15,000 Hz, a range of frequency of more than 250 Hz to about 10,000 Hz, a range of frequency between about 3,000 Hz to about 5,000 Hz, a range of frequency between about 3,000 Hz to about 10,000 Hz, a range of frequency between about 3,000 Hz to about 12,000 Hz, a range of frequency between about 5,000 Hz to about 10,000 Hz, a range of frequency between about 10,000 Hz to about 15,000 Hz, a range of frequency between about 7,000 Hz to about 10,000 Hz, a range of frequency between about 7,000 Hz to about 12,000 Hz, a range of frequency between about 1,000 Hz to about 15,000 Hz, or any other ranges between 250 Hz to about 20,000 Hz or between about 500 Hz to about 20,000 Hz.

Example ranges of frequencies for the first beat signal 130 and the second beat signal 132 may span a few hundred Hz, a few thousand Hz, or a few tens of thousands of Hz.

A range of the frequency for the first beat signal 130 and the second beat signal 132 may be in a lower range, such as more than 250 Hz to about 3,000 Hz, or within a middle range such as between about 3,000 Hz to about 7,000 Hz, or a high range such as between about 7,000 Hz to about 15,000 Hz. Any range or overlapping ranges between more than 250 Hz to about 15,000 Hz may be generated for the frequency of the first beat signal 130 and the second beat signal 132.

Following, the combined beat signal 134 may also be in a range of frequencies, such as a frequency of at least 500 Hz but no more than 20 kHz. The combined beat signal 134 may be any frequency or range of frequencies that would result from interference of the first beat signal 130 and the second beat signal 132 using any frequency for such signals described herein. A few examples of frequencies for the combined beat signal 134 includes 100 Hz, 150 Hz, 200 Hz, 250 Hz, and so on.

Modulating outputs of the first circuit 120, the second circuit 122, the third circuit 124, and the fourth circuit 126 increases the area of the targeted stimulation. A depth of modulation can vary from 0 to 100% and depends on a direction of currents established by the circuits. It has been shown that when two circuits intersect at 90°, the maximum resultant amplitude and the deepest level of modulation is half-way between the two circuits (45° diagonally). Hence, the target area of stimulation can be augmented by modulation of the amplitudes of the outputs of the circuits. Thus, within examples, the interferential current generator 102 adjusts relative amplitudes of the first channel, the second channel, the third channel, and the fourth channel to change an area of application of the combined beat signal 134.

In further examples, the area of application of the combined beat signal 134 can be modulated in three dimensions. For instance, with the first and second channels, the amplitudes of the outputs of the first circuit 120 and the second circuit 122 can be modulated to move the first beat signal 130 up and down along the first plane 136. Similarly, with the third and fourth channels, the amplitudes of the outputs of the third circuit 124 and the fourth circuit 126 can be modulated to move the second beat signal 132 left and right along the second plane 138. Utilizing a stimulation arrangement with all four circuits to create the combined beat signal 134 enables movement of the combined beat signal 134 in any direction. Of the two pairs of circuit, the combined beat signal 134 will tend to shift toward a lower output, such that by decreasing amplitude on one channel, this shifts a center point of the combined beat signal 134 toward that channel. Furthermore, by changing relative amplitudes on all four channels, a depth of the combined beat signal 134 is altered enabling movement of the combined beat signal 134 in a third dimension. Thus, modulation of the amplitudes of the four circuits relative to each other enables movement of the combined beat signal 134 in three dimensions.

The targeted area 128 of stimulation may thus be moved, and a depth of penetration can be altered through modulation of the signals. Furthermore, adjusting frequency of the first signals 104 and the second signals 106 can be performed based on a blood pressure of the subject, so as to achieve an optimal level. As an example, the subject's blood pressure can be monitored, and when stimulation is applied to an optimal area at an optimal amount, an increase or decrease in tracts of the spinal cord can be observed. When tracts are hyper activated, the optimal amount would calm them down, and the subject may not "feel" a change due to a lack of action potential, but a blood pressure of the subject would experience a change that can be monitored and used as a signal to determine the optimal location and amount of stimulation.

Figure 5B:
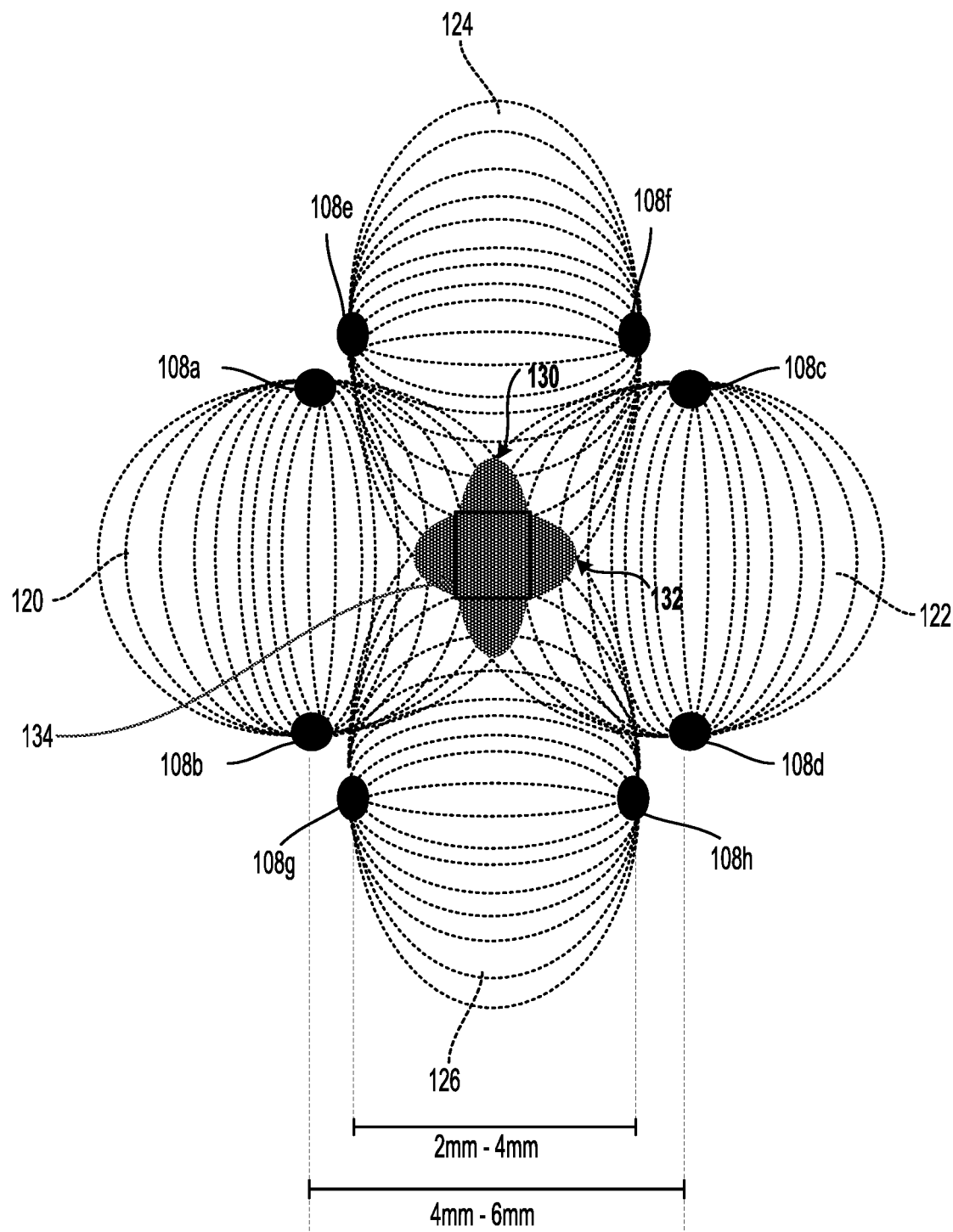
FIG. 5B is a perspective view illustrating an example of another arrangement of the first circuit and the second circuit combined with the third circuit and the fourth circuit, according to an example implementation.

FIG. 5B is a perspective view illustrating an example of an arrangement of the first circuit and the second circuit combined with the third circuit and the fourth circuit, according to an example implementation. In FIG. 5B, spacing between electrodes is illustrated. For example, lateral spacing (across the spinal cord) between the first circuit 120 and the second circuit 122 is between about 4 mm to about 6 mm, and lateral spacing between the pair of implantable electrodes 108e-f for the third circuit 124 and for the pair of implantable electrodes 108g-h for the fourth circuit 126 is between about 2 mm to about 4 mm. In the configuration shown in FIG. 5B, vertical spacing between the third circuit 124 and the fourth circuit 126 is larger than vertical spacing between the pair of implantable electrodes 108a-b and the pair of implantable electrodes 108c-d.

Figure 5C:
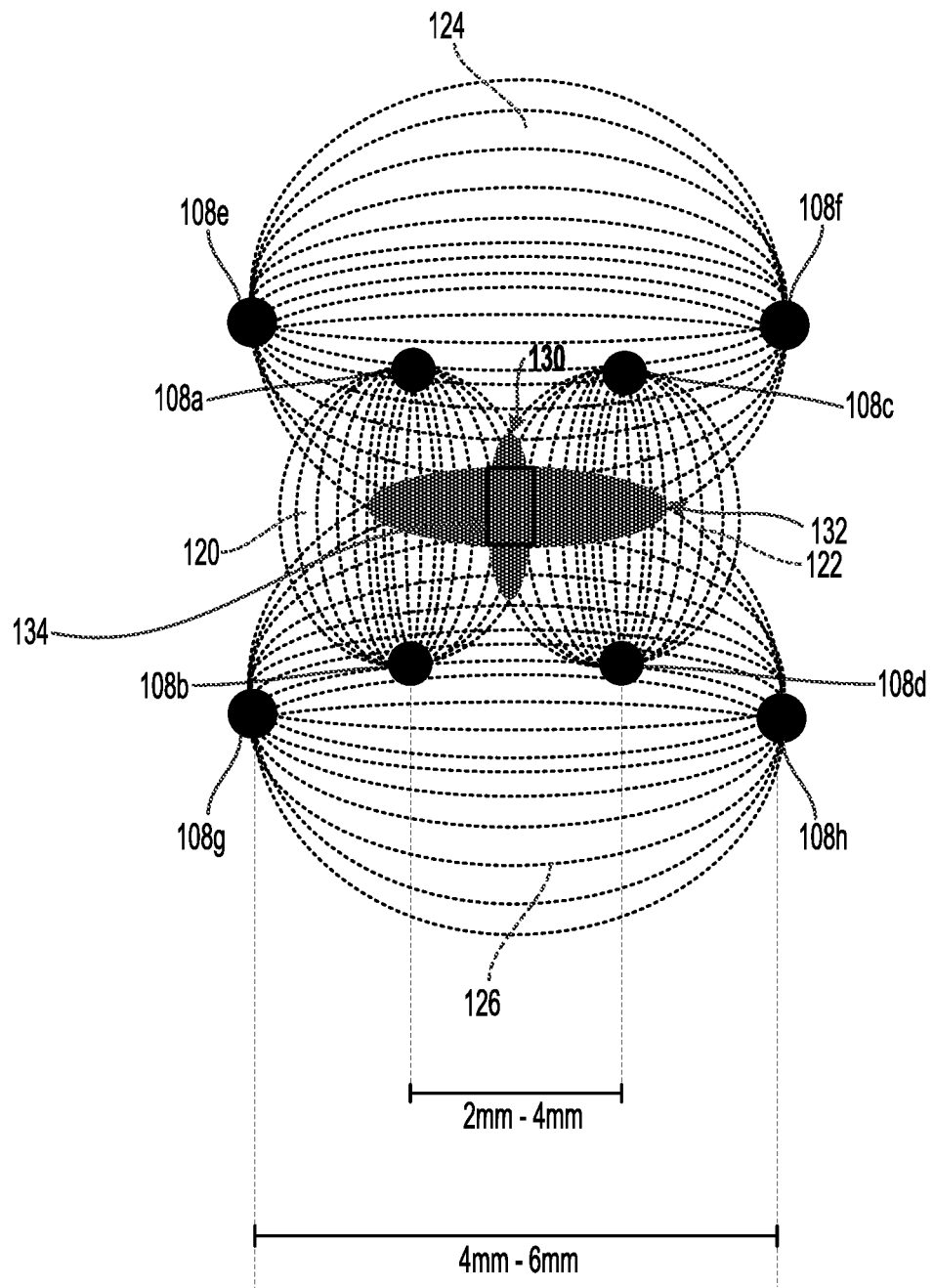
FIG. 5C is a perspective view illustrating an example of yet another arrangement of the first circuit and the second circuit combined with the third circuit and the fourth circuit, according to an example implementation.

FIG. 5C is a perspective view illustrating an example of yet another arrangement of the first circuit and the second circuit combined with the third circuit and the fourth circuit, according to an example implementation. In FIG. 5C, spacing between electrodes is also illustrated. For example, lateral spacing (across the spinal cord) between the first circuit 120 and the second circuit 122 is between about 2 mm to about 4 mm, and lateral spacing between the pair of implantable electrodes 108e-f for the third circuit 124 and for the pair of implantable electrodes 108g-h for the fourth circuit 126 is between about 4 mm to about 6 mm. In the configuration shown in FIG. 5C, vertical spacing between the third circuit 124 and the fourth circuit 126 is larger than vertical spacing between the pair of implantable electrodes 108a-b and the pair of implantable electrodes 108c-d. However, in FIG. 5C, the first circuit 120 and the second circuit 122 are positioned inside a square formed by electrodes of the third circuit 124 and the fourth circuit 126.

In the arrangements shown in FIGS. 5A-5C, electrodes positioned closer together tend to enable higher current density flowing between the electrodes, for example. Thus, an amount of current flowing on channels 1 and 2 can be chosen based on spacing between the electrodes. As seen in FIGS. 5A-5C, the combined beat signal 134 changes in scope and depth of penetration based on the spacing of the electrodes and the circuits.

Figure 6:
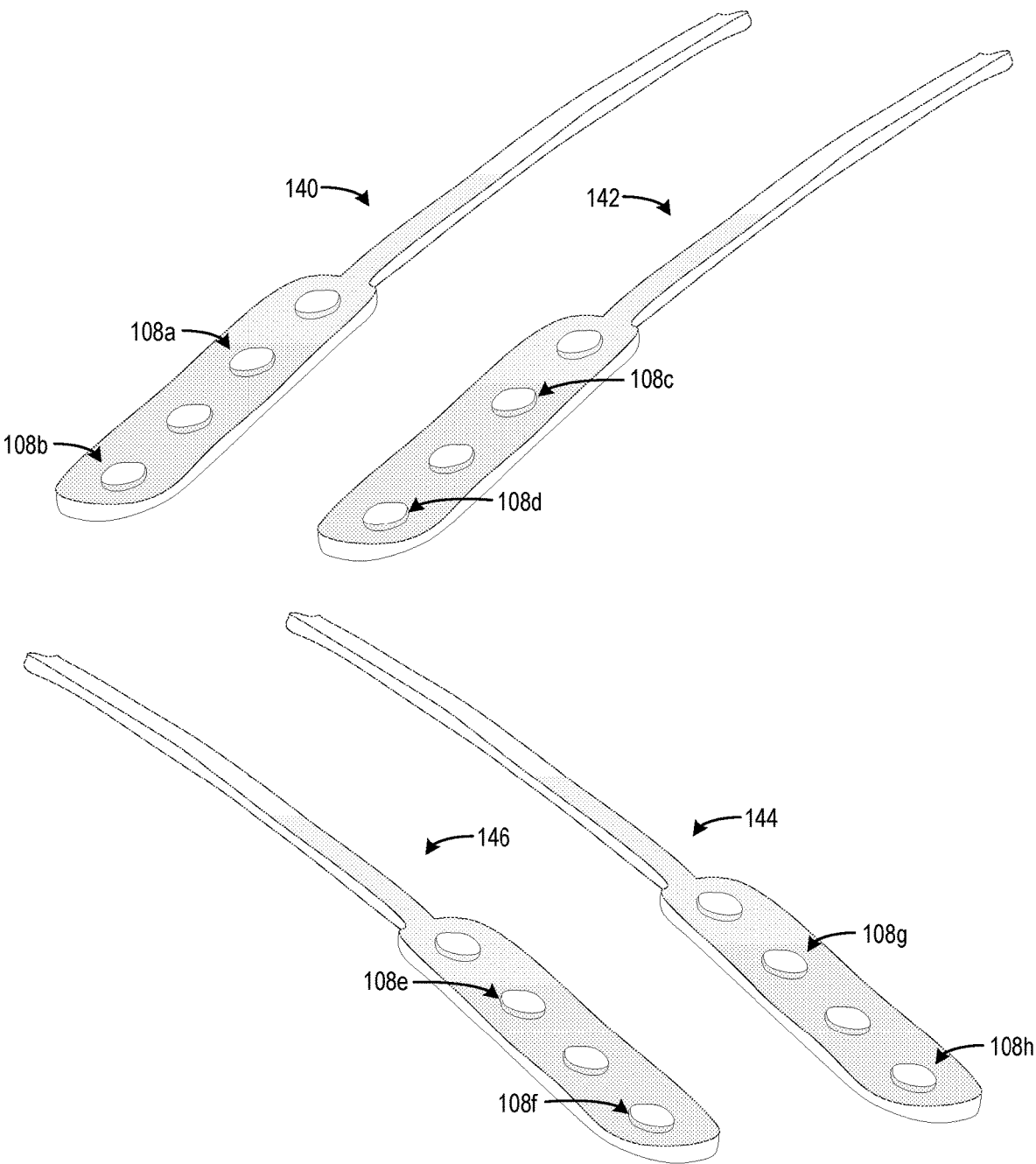
FIG. 6 illustrates example quadripolar leads used for implantation of the implantable electrodes, according to an example implementation.

FIG. 6 illustrates example quadripolar leads used for implantation of the implantable electrodes 108, according to an example implementation. In one example, the first pair of implantable electrodes 108a-b and the second pair of implantable electrodes 108c-d are included on two quadripolar leads 140 and 142, and wherein the third pair of implantable electrodes 108e-f and the fourth pair of implantable electrodes 108g-h are included on two other quadripolar leads 144 and 146. Each quadripolar lead includes four electrodes although only two electrodes are used in each for the configuration shown in FIGS. 5A-5C. The use of quadripolar leads allows a greater target treatment stimulation area of the spinal cord. However, electrical stimulators of the present disclosure may also apply to the use of two bipolar or octapolar lead systems, and other suitable devices. The electrodes could be activated in various combinations and patterns, and not just as shown in the drawings. Thus, in FIG. 6, leads are shown to include four electrodes each, although any number of electrodes may be included such as six, eight, ten, . . . , or up to thirty or thirty-two, for example. Pairs of implantable electrodes are created between the electrodes on the leads. Pairs may be created between electrodes on the same lead (so as to create a parallel configuration).

Separating the electrode pairs may cause a difference in their field strength toward the lateral extremes. Strength of the field is maximum in a center area, however, the field spreads laterally along a target area and is not well confined. The parallel bias and parallel configuration arrangements of the first circuit 120 and the second circuit 122 as well as of the third circuit 124 and the fourth circuit 126 produce a central region where interfering fields are equal and aligned to form a focused modulation beat frequency envelope on the target area 128.

Electrodes are placed and biased so as to produce alignment and equal strength for the component fields at the target area 128 of a desired strong interferential signal. In addition, the two parallel circuit arrangements shown in FIGS. 3 and 4 are placed such that the beat signals of each are unaligned (e.g., perpendicular), or one of the components is weak at other areas for undesired interferential fields (e.g., untargeted areas). Either condition of unalignment or a weak component produces a weak interferential field.

Horizontal separation of the electrodes (or electrode leads) can affect a depth and spreading of penetration. Within examples, the electrodes can be positioned at about 1.5 mm separation, about 2.3 mm separation, or at about 3.9 mm separation for each circuit. The variance of the shape of the field appears optimized at a spacing of about 2.3 mm, however, selective depth of penetration can be achieved using spacing from about 1 mm to about 5 mm, for example.

The arrangement shown in FIGS. 5A-5C requires four different circuits, and for optimal penetration and treatment, it is desired for the frequencies on the four different channels to have at least a threshold differential. For example, frequencies on the respective channels may be required to be at least 1 kHz or more different as less than that can cause too much interference With various spacing providing different levels of treatment, the leads 140/142/144/146 can be optimized in preconfigured arrangements such that a physician chooses the contacts/electrodes for use for given subjects and the geometry is setup for implantation.

FIG. 7 shows a flowchart of an example of a method 200 for spinal cord stimulation treatment using electrical stimulation of the spinal cord, according to an example embodiment. The method shown in FIG. 7 presents an example of a method that, for example, could be used by the stimulator 100 shown in FIG. 1, for example, and may be performed by components of the stimulator 100 in FIG. 1. In some instances, components of the stimulator 100 may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. The method may include one or more operations, functions, or actions as illustrated by one or more of blocks 202-206. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present embodiments. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

At block 202, the method 200 includes positioning at least eight implantable electrodes 108a-h to a dura matter 110 in an epidural space 112 proximate to a subject's spinal cord 114 at predetermined locations so that (i) a first circuit 120 is created between a first electrode 108a and a second electrode 108b of the eight implantable electrodes on a first channel, (ii) a second circuit 122 is created between a third electrode 108c and a fourth electrode 108d of the eight implantable electrodes on a second channel, (iii) a third circuit 124 is created between a fifth electrode 108e and a sixth electrode 108f of the eight implantable electrodes on a third channel, and (iv) a fourth circuit 126 is created between a seventh electrode 108g and an eighth electrode 108h of the eight implantable electrodes on a fourth channel.

Within examples, positioning the implantable electrodes includes positioning a first pair of implantable electrodes 108a-b to a dura matter in an epidural space proximate to a subject's spinal cord at predetermined locations, positioning a second pair of implantable electrodes 108c-d to the dura matter in the epidural space proximate to the subject's spinal cord at predetermined locations, positioning a third pair of implantable electrodes 108e-f to a dura matter in an epidural space proximate to a subject's spinal cord at predetermined locations, and positioning a fourth pair of implantable electrodes 108g-h to a dura matter in an epidural space proximate to a subject's spinal cord at predetermined locations.

Within examples, proximate to the spinal cord can vary due to variances of distance between dura and spinal cord within different people. For example, cerebral spinal fluid and other internal layers are present between the dura and spinal cord, and a distance can vary also due to whether a person is sitting, standing, or laying down (e.g., as the spinal cord moves within the cerebral spinal fluid). Thus, proximate to the spinal cord indicates positioned in the dura matter in the epidural space, for example.

In addition, distances from the dura to the spinal cord are not uniform at different vertebral levels. In an example, a distance across epidural space varies, and can be in a range of 1-1.5 mm a cervical region, 2.5-3 mm in an upper thoracic region, 4-5 mm in a lower thoracic region, and 5-6 mm in a lumbar region.

Other examples have shown that distance from the dura to spinal cord has a range of about 5.9±1.6 mm at the thoracic levels $T_{6-7}$, range of about 5.0±1.6 mm at the thoracic levels $T_{9-10}$, and range of about 3.6±1.2 mm at the thoracic levels $L_{1-2}$.

In still further examples, distances from the dura matter to the spinal cord at the different thoracic levels may be in ranges as shown in the table below.

| Intervertebral Level | Distance from dura matter to spinal cord |
|---|---|
| $T_{1-2}$ | 2.91 ± 0.90 mm |
| $T_{2-3}$ | 3.52 ± 1.12 mm |
| $T_{3-4}$ | 3.84 ± 1.23 mm |
| $T_{4-5}$ | 4.15 ± 1.42 mm |
| $T_{5-6}$ | 4.22 ± 1.43 mm |
| $T_{6-7}$ | 4.10 ± 1.46 mm |
| $T_{7-8}$ | 3.87 ± 1.26 mm |
| $T_{8-9}$ | 3.35 ± 1.17 mm |
| $T_{9-10}$ | 2.96 ± 1.05 mm |
| $T_{10-11}$ | 2.83 ± 0.92 mm |
| $T_{11-12}$ | 2.51 ± 0.87 mm |

Arranging the electrodes proximate to the spinal cord can include, in some examples, arranging the electrodes to be within 0.5 mm of the corresponding region along the spinal cord. In other examples, the electrodes are arranged proximate to the spinal cord when the electrodes are positioned anywhere within boundaries of a corresponding region along the spinal cord as defined by spacing between the regions (e.g., e.g., cervical, upper thoracic, lower thoracic, or lumbar). In still other examples, the electrodes are arranged proximate to the spinal cord when the electrodes are positioned in the dura matter and within a distance to the spinal cord that is in a range of a thickness from the dura matter to the spinal cord for the respective region along the spinal cord in which the electrode is positioned.

In some examples, the first pair of implantable electrodes 108a-b and the second pair of implantable electrodes 108c-d are included on two quadripolar leads 140 and 142, and the third pair of implantable electrodes 108e-f and the fourth pair of implantable electrodes 108g-h are included on two other quadripolar leads 144 and 146.

In further examples, the method 200 also includes supplying digital signal pulses to a digital signal processor via a pulse generator, the digital signal processor processing the digital signal pulses to approximate a sine-wave-like output waveform, and transmitting the sine-wave-like output waveform as the first signals and the second signals.

At block 204, the method 200 includes transmitting first signals 104 through the first circuit 120 and the second circuit 122 so that the first signals 104 interfere with each other to produce a first beat signal 130. In some examples, this includes transmitting signals having a base frequency of about 15 kHz on the first channel, transmitting signals having a base frequency of about 10 kHz on the second channel, and signals on the first channel and the second channel interfere with each other to produce the first beat signal having a beat frequency of about 5 kHz.

At block 206, the method 200 includes transmitting second signals 106 through the third circuit 124 and the fourth circuit 126 so that the second signals 106 interfere with each other to produce a second beat signal 132. In some examples, this includes transmitting signals transmitting signals having a base frequency of about 20 kHz on the third channel, transmitting signals having a base frequency of about 14.9 kHz on the fourth channel, and signals on the third channel and the fourth channel interfere with each other to produce the second beat signal having a beat frequency of about 5.1 kHz.

Within examples, each of the first beat signal 130 and the second beat signal 132 have beat frequencies over 5 kHz.

Following, interaction of the first beat signal 130 and the second beat signal 132 results in a combined beat signal 134 proximate to the subject's spinal cord 114. Within examples, the first circuit 120, the second circuit 122, the third circuit 124, and the fourth circuit 126 are arranged in an approximate square configuration, and the combined beat signal 134 results in a center portion of the approximate square configuration. For example, interaction of the first beat signal 130 and the second beat signal 132 results in the combined beat signal 134 being about 100 Hz. In further examples, the combined beat signal 134 has a frequency of at least 500 Hz but no more than 20 kHz.

In some examples, the method 200 also includes modulating the area of application of the combined beat signal 134 in three dimensions.

In still further examples, the method 200 includes adjusting frequency of the first signals 104 and the second signals 106 based on a blood pressure of the subject.

Figure 8A:
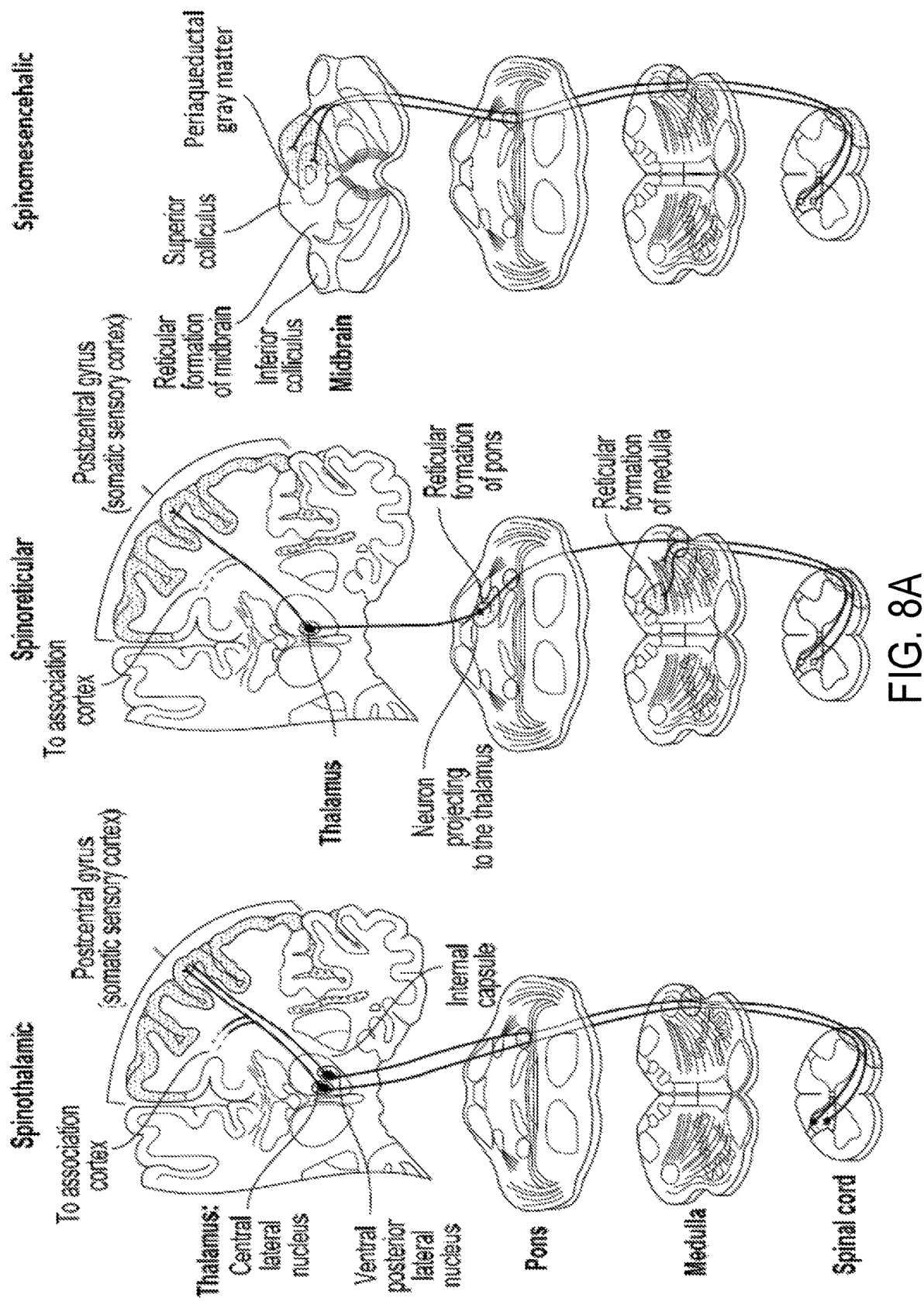
FIG. 8A illustrates an example of the spinothalamic, spinoreticular, spinomesencephalic tracts, according to an example implementation.
Figure 8C:
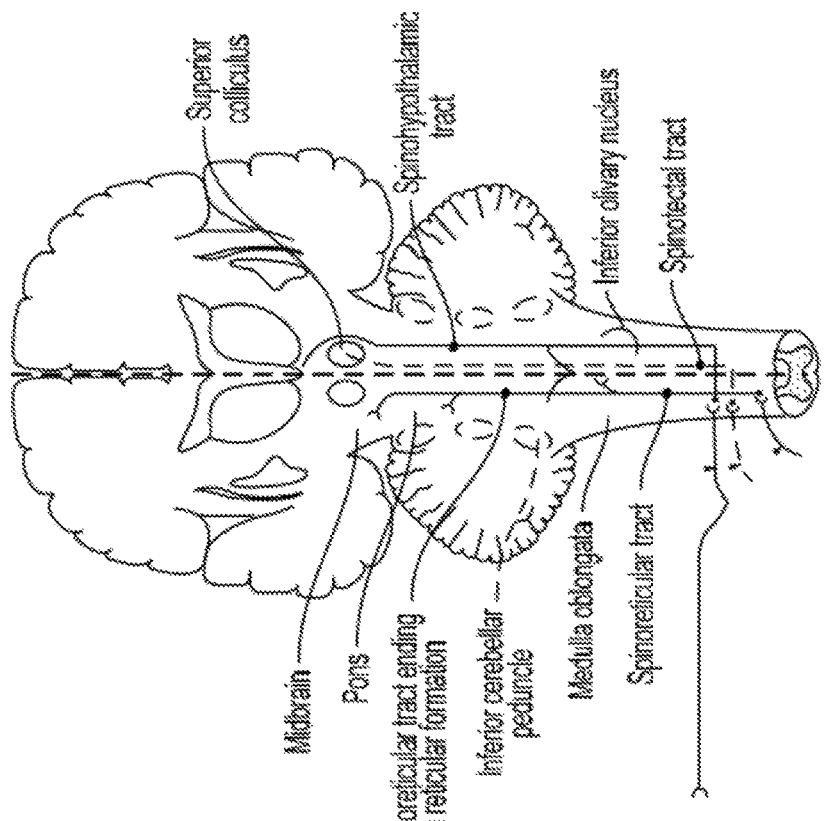
FIG. 8C illustrates an example of the spinohypothalamic tract, according to an example implementation.
Figure 8B:
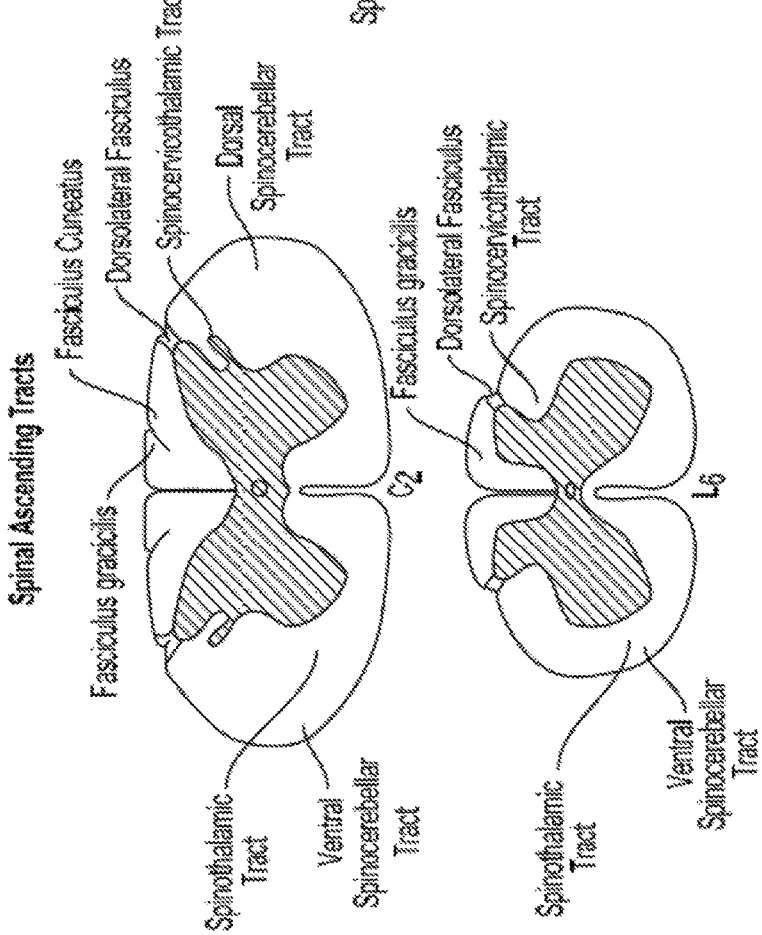
FIG. 8B illustrates an example of the cerviocothalamic tract, according to an example implementation.

Within examples, forming a beat signal at a frequency at ranges described herein allows the signal to reach deeper into the dorsal column, and enables the signal to affect the membrane potential on other deeper structures of the spinal cord. Nociceptive information is transmitted from the spinal cord to the thalamus via five major ascending pathways including the spinothalamic, spinoreticular, spinomesencephalic, cerviocothalamic and spinohypothalamic tracts. FIG. 8A illustrates an example of the spinothalamic, spinoreticular, spinomesencephalic tracts, FIG. 8B illustrates an example of the cerviocothalamic tract, and FIG. 8C illustrates an example of the spinohypothalamic tract, according to an example implementation. Using examples herein, the combined beat signal may be directionally controlled deep into the subject's tissue proximate to one or more of these ascending pathways, and avoiding the at least one beat signal remaining in and shunting through cerebrospinal fluid proximate the subject's dorsal column.

Some standard spinal cord stimulation for pain uses low frequencies of 40 to 100 Hz for beat signals, and focuses on maximizing stimulation of the dorsal column. Other systems use medium frequency stimulation and do not generate action potentials, but rather produce "non-paresthesia" stimulation of the spinal cord. In other words, the patient does not feel any buzzing or stimulation in the areas of pain. The onset of action takes very long, and usually takes effect from 12 to 16 hours after is initiated. Because the patient does not feel the stimulation and action potentials are not being generated, the logical mechanism of action may be that this medium frequency output is affecting the membrane potential of the outer areas of the cord and potentially decreasing hyperactivity of the neurons which would be perceived as less pain.

Within examples herein, the combined beat signal proximate to the subject's spinal cord can be modulated to produce a paresthesia-type beat signal, such that a subject may feel the signal. In this way, the subject can help with placement of the electrodes and stimulation of a target area is properly performed.

Additionally, as described above, electrodes can be placed to a dura matter in an epidural space proximate the subject's spinal cord to produce at least one beat signal proximate to the subject's spinal cord, and avoiding the at least one beat signal remaining in and shunting through cerebrospinal fluid proximate the subject's dorsal column through directional control. Spacing of the electrodes further enables directional control of the beat signal.

The five major ascending pathways including the spinothalamic, spinoreticular, spinomesencephalic, cerviocothalamic and spinohypothalamic tracts are not the main targets of older standard SCS because they cannot generate fields deep enough in the tissue without causing undesirable side effects and shunting of the stimulation.

Example interferential SCS stimulation described herein with a beat frequency of more than 250 Hz to about 15 k Hz (e.g., such as in the range of 10 kHz to 15 kHz) is able to generate higher amplitude envelopes of current that can be directed to other areas of the cord and have effects on the ascending tracts that may not be able to be accomplished with standard SCS stimulation because the standard SCS cannot generate such effective beat frequencies and direct the higher amplitude envelopes. The higher beat frequencies (250 Hz to 15 kHz) would have the added benefit of overcoming capacitive resistance of interfaces between different tissue types and tissue membranes and allow passage of sub-threshold and threshold current to deeper layers of the spinal cord.

Figure 9:
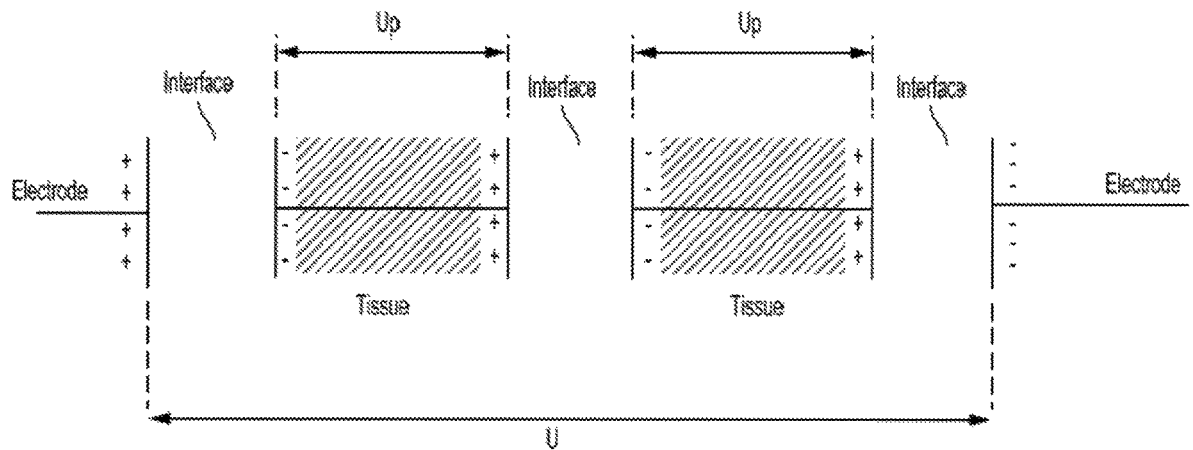
FIG. 9 illustrates an example diagram for capacitive resistance of tissue, according to an example implementation.

FIG. 9 illustrates an example diagram for capacitive resistance of tissue, according to an example implementation. Separate tissue may be conceptually considered as having an interface between the tissue as shown. In FIG. 9, U is an applied voltage, and $U_p$ is a potential difference. The potential difference, $U_p$, is counter to the applied voltage, U, and develops a counter-voltage that is conceptually considered a reactance or capacitive resistance, X. A marked drop of the reactance of tissue interfaces at increased frequency is shown in the following formula:

$$X = \frac{1}{2\pi f C}$$

where X is capacitive resistance (reactance), f is frequency of the current, and C is polarization capacitance of the tissue.

For a 100 Hz alternating current, and C of $10^{-6}$, the reactance X is about 1600 ohms. For a 10 k Hz alternating current, the reactance X is about 16 ohms.

An interferential system of SCS that generates a higher beat frequency from 250 Hz to 15 kHz could penetrate deeper by generating a beat of 10 kHz to 15 kHz at a sub-threshold level for causing action potentials, and is sufficient to affect membrane potentials of other deeper structures of the cord including the five major ascending pathways directly rather than through dorsal column stimulation. Affecting these tracts and other deep structures of the cord can provide normalizing properties and potentially sooth hyperactivity in the tracts providing positive regulation of multiple symptoms other than pain such as cardiovascular, neuroendocirine, respiratory and emotional functions.

With deeper penetration through further levels of capacitive resistance, using eight implantable electrodes with signals resulting in the first beat signal 130 and the second beat signal 132 both over 5 kHz, this results in a combined beat signal 134 that will form deeper in tissue. For example, for beat signals have frequencies around 250 Hz, when these signals hit a surface of the dorsal column, there will be some penetration, but there is also a counter-voltage pushback. However, with beat signals having frequencies at 2 kHz or higher, for example, these signals overcome the counter-voltage. Higher frequency beat signals spread out further as well.

The stimulator 100 described herein may be fully implanted into a subject, or portions of the stimulator 100 may be implanted and portions remain exterior of the subject. As an example, the electrodes may be implantable, as described, and the interferential current generator and power source can be external and coupled to the implanted electrodes through wires. In other examples, coupling may occur through a wireless link (e.g., radio frequency (RF) link) from the current generator to the electrodes, such that the electrodes are implanted and the current generator is not implanted. The RF carrier frequency can be in the MHz, GHz or THz range and will induce a current in an implanted receiver that is linked or connected to the implantable electrodes. The RF carrier frequency can range from about 1 MHz through about 20 THz.

In still other examples, the interferential current generator is implantable in the subject (and a power source connected to the interferential current generator may be implanted as well), and the electrodes are further implanted. The interferential current generator may be implanted near or in the brachial plexus, or near or underneath the 12$^{th}$ rib bone, for example.

Figure 10:
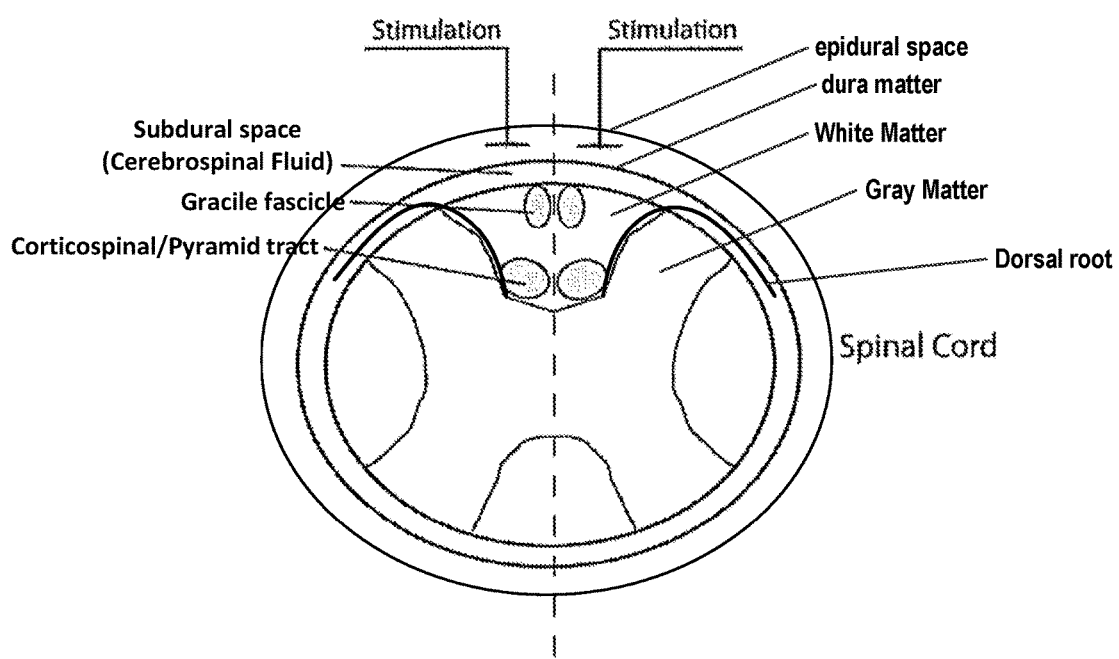
FIG. 10 illustrates the *Gracile* nucleus and Pyramid tract as ascending and descending tracts in the dorsal column of the spinal cord, according to an example implementation.

Within examples, using the stimulator 100 in FIG. 1 for spinal cord stimulation (SCS) provides deep stimulation for effective pain relief. Effective pain relief can be achieved by activating one of the ascending pathways including the spinothalamic, spinoreticular, spinomesencephalic, cerviocothalamic and spinohypothalamic tracts, as described above. In addition, activation of the *Gracile* nucleus and Pyramid tract in the spinal cord may provide effective relief. FIG. 10 illustrates the *Gracile* nucleus and Pyramid tract as ascending and descending tracts in the dorsal column of the spinal cord, according to an example implementation. The spinal cord is encased in a thick membrane called the dura mater, and inside a layer of the dura mater is cerebrospinal fluid, as shown in FIG. 10.

The cerebrospinal fluid is conductive, and stimulation that spreads through the fluid can cause pain if the current density becomes too high near the dorsal root ganglia that lie along a vertebral column by the spine. It is desired to provide deep stimulation through the dura mater of the spinal cord for activating the *Gracile* nucleus and Pyramid and other portions of the Dorsal Column using low levels of stimulation so as to avoid spreading of stimulation through the cerebrospinal fluid.

Using an interferential current SCS, stimulation may be provided deep through the dura mater with low current levels, thus lowering the threshold of activation of the *Gracile* nucleus and Pyramid. With spinal cord stimulation, if current is simply increased, the effect may be to spread stimulation through the cerebrospinal fluid, resulting in stimulation of the dorsal root ganglia, which causes chest and thoracic pain. Using an interferential current SCS method to directionally control stimulation, low levels of stimulation can be provided, and deep penetration through the dura mater can be achieved without spreading of the stimulation and resulting side effects.

By the term "about" and/or the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

It should be emphasized that the above-described embodiments of the present disclosure are merely possible examples of implementations set forth for a clear understanding. Many variations and modifications may be made to the above-described embodiment(s) without departing substantially from the principles of the disclosure. All such modifications and variations are intended to be included herein within the scope of this disclosure.

What is claimed is:

1. A method for spinal cord stimulation treatment using electrical stimulation of the spinal cord, the method comprising:
   positioning at least eight implantable electrodes to a dura matter in an epidural space proximate to a subject's spinal cord at predetermined locations so that (i) a first circuit is created between a first electrode and a second electrode of the eight implantable electrodes on a first channel, (ii) a second circuit is created between a third electrode and a fourth electrode of the eight implantable electrodes on a second channel, (iii) a third circuit is created between a fifth electrode and a sixth electrode of the eight implantable electrodes on a third channel, and (iv) a fourth circuit is created between a seventh electrode and an eighth electrode of the eight implantable electrodes on a fourth channel;
   transmitting first signals through the first circuit and the second circuit so that the first signals interfere with each other to produce a first beat signal; and
   transmitting second signals through the third circuit and the fourth circuit so that the second signals interfere with each other to produce a second beat signal,
   wherein interaction of the first beat signal and the second beat signal results in a combined beat signal proximate to the subject's spinal cord.

2. The method of claim 1, wherein transmitting the first signals through the first circuit and the second circuit so that the first signals interfere with each other to produce the first beat signal comprises:
   transmitting signals having a base frequency of about 15 kHz on the first channel; and
   transmitting signals having a base frequency of about 10 kHz on the second channel,
   wherein signals on the first channel and the second channel interfere with each other to produce the first beat signal having a beat frequency of about 5 kHz.

3. The method of claim 1, wherein transmitting the second signals through the third circuit and the fourth circuit so that the second signals interfere with each other to produce the second beat signal comprises:
   transmitting signals having a base frequency of about 20 kHz on the third channel; and
   transmitting signals having a base frequency of about 14.9 kHz on the fourth channel,
   wherein signals on the third channel and the fourth channel interfere with each other to produce the second beat signal having a beat frequency of about 5.1 kHz.

4. The method of claim 1, wherein interaction of the first beat signal and the second beat signal results in the combined beat signal being about 100 Hz.

5. The method of claim 1, wherein each of the first beat signal and the second beat signal have beat frequencies over 5 kHz.

6. The method of claim 1, wherein the first circuit and the second circuit are arranged parallel to each other along a first plane; and
   wherein the third circuit and the fourth circuit are arranged parallel to each other along a second plane; and
   wherein the first plane is substantially perpendicular to the second plane.

7. The method of claim 1, wherein the first circuit and the second circuit are arranged parallel to the spinal cord, and
   wherein the third circuit and the fourth circuit are arranged perpendicular to the spinal cord.

8. The method of claim 1, wherein the first circuit, the second circuit, the third circuit, and the fourth circuit are arranged in an approximate square configuration, and the combined beat signal results in a center portion of the approximate square configuration.

9. The method of claim 1, wherein positioning at least eight implantable electrodes to a dura matter in an epidural space proximate to a subject's spinal cord at predetermined locations comprises:

positioning a first pair of implantable electrodes to a dura matter in an epidural space proximate to a subject's spinal cord at predetermined locations;

positioning a second pair of implantable electrodes to the dura matter in the epidural space proximate to the subject's spinal cord at predetermined locations;

positioning a third pair of implantable electrodes to a dura matter in an epidural space proximate to a subject's spinal cord at predetermined locations; and positioning a fourth pair of implantable electrodes to a dura matter in an epidural space proximate to a subject's spinal cord at predetermined locations.

10. The method of claim 9, wherein the first pair of implantable electrodes and the second pair of implantable electrodes are included on two quadripolar leads, and wherein the third pair of implantable electrodes and the fourth pair of implantable electrodes are included on two other quadripolar leads.

11. The method of claim 1, wherein the combined beat signal has a frequency of at least 500 Hz but no more than 20 kHz.

12. The method of claim 1, further comprising:
modulating relative amplitudes of the first channel, the second channel, the third channel, and the fourth channel to change an area of application of the combined beat signal.

13. The method of claim 12, further comprising:
modulating the area of application of the combined beat signal in three dimensions.

14. The method of claim 1, further comprising:
adjusting frequency of the first signals and the second signals based on a blood pressure of the subject.

15. The method of claim 1, further comprising:
supplying digital signal pulses to a digital signal processor via a pulse generator;
the digital signal processor processing the digital signal pulses to approximate a sine-wave-like output waveform; and
transmitting the sine-wave-like output waveform as the first signals and the second signals.

16. An electrical stimulator for spinal cord stimulation treatment, comprising:
an interferential current generator which generates an interferential alternating current output comprising first signals and second signals; and
at least eight implantable electrodes, wherein each electrode has a first and a second end, wherein the first ends are coupled to the interferential current generator and the second ends are configured to be implanted to a dura matter in an epidural space at predetermined locations proximate to a subject's spinal cord so that (i) a first circuit is created between a first electrode and a second electrode of the eight implantable electrodes on a first channel, (ii) a second circuit is created between a third electrode and a fourth electrode of the eight implantable electrodes on a second channel, (iii) a third circuit is created between a fifth electrode and a sixth electrode of the eight implantable electrodes on a third channel, and (iv) a fourth circuit is created between a seventh electrode and an eighth electrode of the eight implantable electrodes on a fourth channel, wherein first signals are transmitted through the first circuit and the second circuit so that the first signals interfere with each other to produce a first beat signal, wherein second signals are transmitted through the third circuit and the fourth circuit so that the second signals interfere with each other to produce a second beat signal, and wherein interaction of the first beat signal and the second beat signal results in a combined beat signal proximate to the subject's spinal cord.

17. The electrical stimulator of claim 16, wherein the first circuit and the second circuit are arranged parallel to each other along a first plane;
wherein the third circuit and the fourth circuit are arranged parallel to each other along a second plane; and
wherein the first plane is perpendicular to the second plane.

18. The electrical stimulator of claim 16, wherein the first circuit and the second circuit are arranged parallel to the spinal cord, and
wherein the third circuit and the fourth circuit are arranged perpendicular to the spinal cord.

19. The electrical stimulator of claim 16, wherein the interferential current generator adjusts relative amplitudes of the first channel, the second channel, the third channel, and the fourth channel to change an area of application of the combined beat signal.

20. The electrical stimulator of claim 16, wherein the interferential current generator comprises:
a pulse generator that generates digital signal pulses; and
a digital signal processor connected to said pulse generator that processes the digital signal pulses to approximate a sine-wave-like output waveform.

* * * * *